(12) United States Patent
Houben et al.

(10) Patent No.: US 7,627,368 B2
(45) Date of Patent: Dec. 1, 2009

(54) METHOD AND APPARATUS FOR ATRIAL ARRHYTHMIA DETECTION

(75) Inventors: Richard P.M. Houben, Lanaken (BE); Vincent Larik, Kerkrade (NL); Tim D.J. Jongen, Heerlen (NL)

(73) Assignee: Medtronic, Inc., Minneapolis, MN (US)

( * ) Notice: Subject to any disclaimer, the term of this patent is extended or adjusted under 35 U.S.C. 154(b) by 508 days.

(21) Appl. No.: 11/616,993

(22) Filed: Dec. 28, 2006

(65) Prior Publication Data

US 2008/0161703 A1 Jul. 3, 2008

(51) Int. Cl.
*A61B 5/0456* (2006.01)
*A61B 5/046* (2006.01)
*A61B 5/0464* (2006.01)
*A61B 5/0468* (2006.01)

(52) U.S. Cl. .................. 600/515; 600/516; 600/518
(58) Field of Classification Search ................. 600/515, 600/516, 518
See application file for complete search history.

(56) References Cited

U.S. PATENT DOCUMENTS

| 5,720,295 | A | 2/1998 | Greenhut et al. |
|---|---|---|---|
| 5,772,604 | A | 6/1998 | Langberg et al. |
| 6,490,479 | B2 | 12/2002 | Bock |
| 6,496,731 | B1 | 12/2002 | Lovett |
| 2002/0065473 | A1 | 5/2002 | Wang et al. |
| 2006/0247547 | A1 | 11/2006 | Sarkar et al. |
| 2006/0247548 | A1 | 11/2006 | Sarkar et al. |

*Primary Examiner*—Carl H Layno
*Assistant Examiner*—Yun Haeng Lee
(74) *Attorney, Agent, or Firm*—Stephen W. Bauer (57) ABSTRACT

A medical device performs a method for detecting atrial arrhythmias. A signal including ventricular cycle length information is sensed in a patient and used to determine each difference between successive ventricular cycle lengths occurring during a predetermined time period. Each succeeding difference is stored as a data point in a histogram, and a metric of variability of the data points of the histogram is determined. An atrial arrhythmia is detected in response to the metric crossing a threshold. The threshold is determined in response to the number of ventricular cycle lengths occurring during the predetermined time period.

21 Claims, 6 Drawing Sheets

METHOD AND APPARATUS FOR ATRIAL ARRHYTHMIA DETECTION

TECHNICAL FIELD

The invention relates generally to implantable medical devices and, in particular, to methods for detecting atrial arrhythmias using ventricular cycle lengths.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

In the past, atrial arrhythmias have been largely undertreated due to the perception that these arrhythmias are relatively benign. As more serious consequences of persistent atrial arrhythmias have come to be understood, such as an associated risk of relatively more serious ventricular arrhythmias and stroke, there is a growing interest in monitoring and treating atrial arrhythmias.

Methods for discriminating cardiac arrhythmias have been developed for use in dual chamber implantable devices wherein both an atrial EGM signal and a ventricular EGM signal are available. Discrimination of arrhythmias can rely on event intervals (e.g., PP intervals and RR intervals during cardiac cycles), event patterns, and EGM morphology. Such methods have been shown to reliably discriminate ventricular arrhythmias from supra-ventricular arrhythmias. However, in single chamber implantable devices, subcutaneous implantable devices, and external monitoring devices, an adequate atrial EGM signal is not always available for use in detecting and discriminating atrial arrhythmias.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In various embodiments of the invention, ventricular signals are used for determining successive ventricular cycle lengths for use in detecting atrial arrhythmias. The atrial arrhythmia detection methods do not require an atrial signal source. The methods presented herein may be embodied in either software or in firmware in implantable or external medical devices. Such devices include implantable monitoring devices having cardiac EGM monitoring capabilities and associated EGM sense electrodes, which may be intracardiac, epicardial, or subcutaneous electrodes. The methods provided by the present invention can also be incorporated into software or in firmware of implantable medical devices having therapy delivery capabilities, such as single chamber or bi-ventricular pacing systems or ICDs that sense the R-waves in the ventricles and deliver an electrical stimulation therapy to the ventricles. Methods provided by the present invention may also be incorporated into the firmware or software of external monitors having ECG electrodes coupled to the patient's skin to detect R-waves, e.g. Holter monitors, or within computerized systems that assess pre-recorded ECG or EGM data. Embodiments of the invention may further be implemented in a patient monitoring system, such as a centralized computer system which processes data sent to it by implantable or wearable monitoring devices.

It is also recognized that embodiments of the invention may be implemented in internal or external monitoring systems that include sensors of ventricular activity from which ventricular cycle length (VCL) measurements can be made. Practice of the present invention is not limited to the use of EGM or ECG signals for measuring VCLs. Other signals, such as pressure signals, blood oximetry signals, flow signals, ventricular wall motion signals, volume-related impedance signals, or other physiological signals responsive to the ventricular cycle, can be used for measuring VCLs. Generally, VCL measurements should have a resolution on the order of about 1 to 20 ms to allow for atrial arrhythmia detection based on VCL irregularity metrics, however, aspects of the invention may be implemented in systems having lower resolution of VCL measurements.

Figure 1:
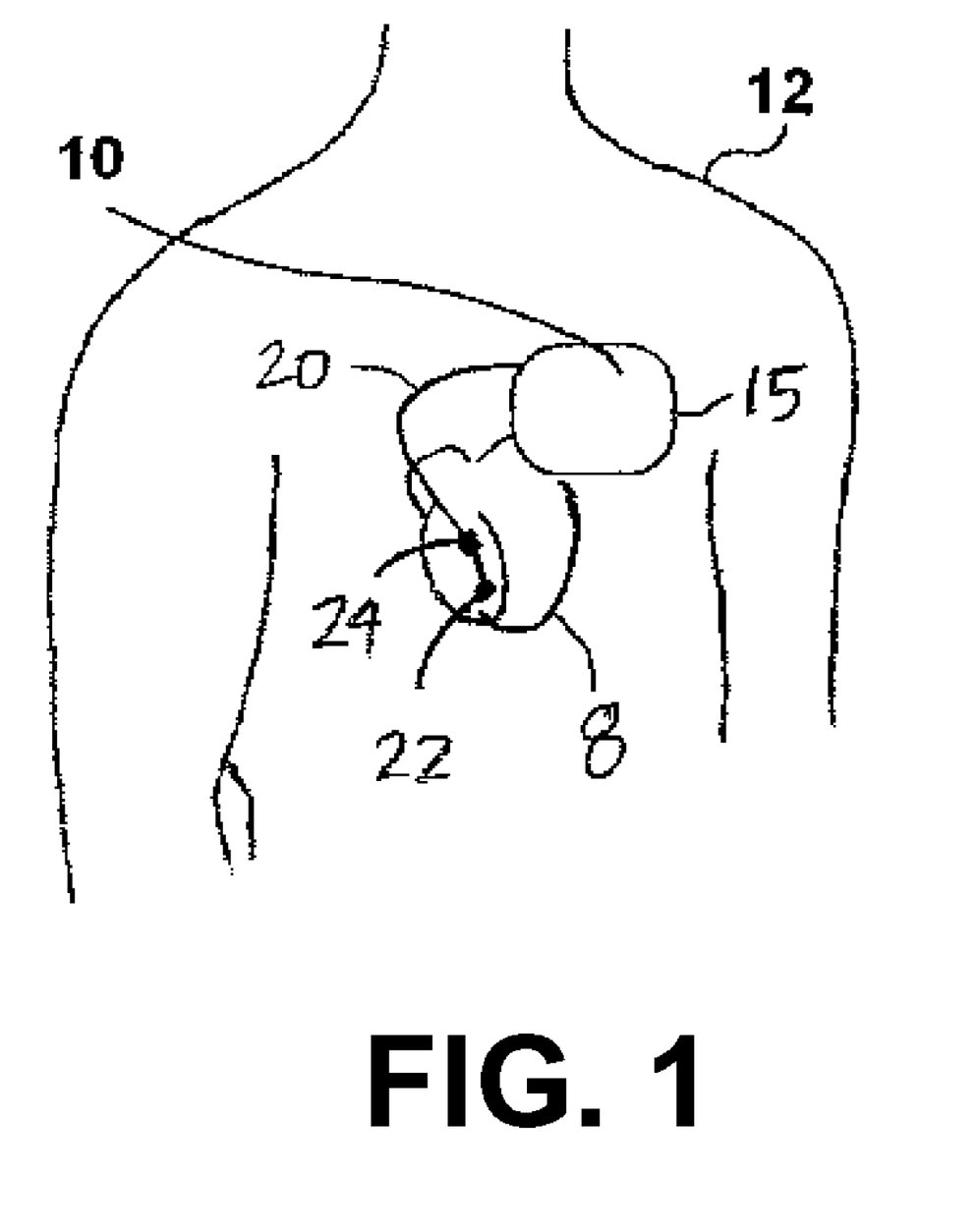
FIG. 1 is an illustration of an implantable medical device (IMD) implanted in a patient and coupled to the patient's heart via a ventricular lead.

FIG. 1 is an illustration of an implantable medical device (IMD) implanted in a patient and coupled to the patient's heart via a ventricular lead. The simplified illustration of IMD 10 may represent a variety of IMDs such as a cardiac pacemaker, implantable cardioverter defibrillator, hemodynamic monitor, ECG recorder, or a drug delivery device. IMD 10 may be coupled to one or more fluid delivery catheters or electrical leads 20. In the embodiment shown, lead 40 is used for carrying one or more electrodes and/or other physiological sensors used for monitoring one or more physiological signals and delivering electrical stimulation therapies to the patient's heart 8. IMD 10 may alternatively be embodied as a leadless device wherein sensors and/or electrodes are incorporated in or on the housing of IMD 10. Examples of devices incorporating leadless electrodes are generally disclosed in U.S. Pat. No. 6,522,915 (Ceballos et al.) and U.S. Pat. No. 5,987,352 (Klein et al.), both of which patents are incorporated herein by reference in their entirety.

Lead 40 is a right ventricular lead including one or more electrodes 42 and/or sensors 44. Electrode 42 may be used in conjunction with IMD housing 15 for sensing ventricular EGM signals. Lead 40 may be provided with a second electrode for bipolar sensing of EGM signals. In one embodiment of the invention, sensor 44 is used for sensing a ventricular pressure signal which may be used in some embodiments of the invention for determining VCLs.

Figure 2:
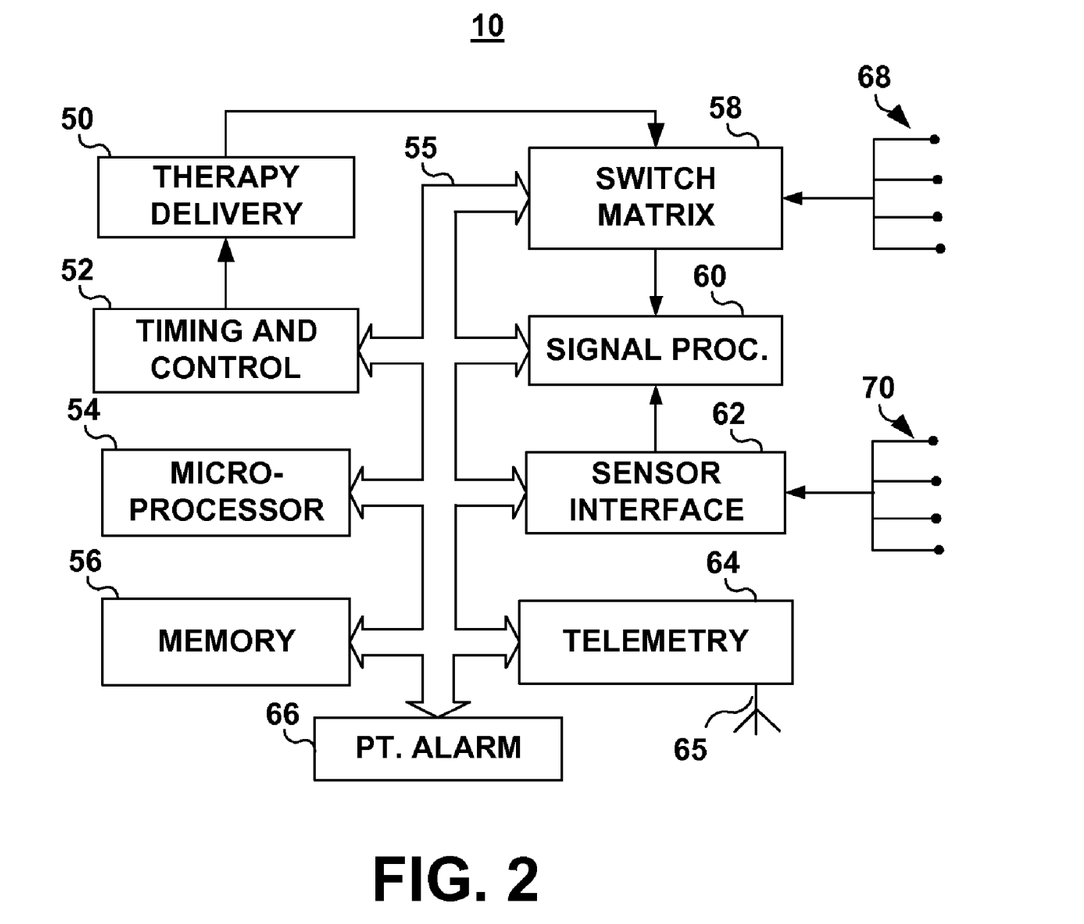
FIG. 2 is a functional block diagram of an IMD.

FIG. 2 is a functional block diagram of IMD 10. IMD 10 generally includes timing and control circuitry 52 and an operating system that may employ microprocessor 54 or a digital state machine for timing sensing and therapy delivery functions and controlling other device functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may be lead-based electrodes, leadless electrodes incorporated on IMD 10, and/or the IMD housing configured for use as a can or case electrode. Electrodes 68 are used for sensing electrical ventricular signals and may be used for sensing other signals within the body, such as impedance signals. Cardiac electrical signals are sensed using any of electrodes 68 for detecting and diagnosing heart rhythms and may be used for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog to digital converter. Electrical signals may then be used by microprocessor 54 for detecting physiological events, such as detecting and discriminating cardiac arrhythmias.

IMD 10 may include other physiological sensors 70. Physiological sensors 70 may include pressure sensors, accelerometers, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, and/or patient activity. Monitored signals may be used for diagnosing a patient condition or for sensing the need for delivering a therapy under control of the operating system.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. Memory 56 is used to store operating commands and data for controlling device operation and for later retrieval to diagnose device function or patient condition. In accordance with the various embodiments of the present invention, parameter values and thresholds used for detecting atrial arrhythmias from a ventricular signal are stored in memory 56. A portion of memory 56 is allocated for storing ventricular cycle length data over predetermined intervals of time and used for determining a metric of VCL irregularity as will be described herein.

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit. Data from IMD 10 may be transmitted to a centralized patient database to enable a physician to monitor the patient from a remote location.

IMD 10 may include patient alarm circuitry 66 for generating audible tones, a perceptible vibration, muscle stimulation or other sensory stimulation for notifying the patient that an alarm condition has been detected by IMD 10.

Figure 3:
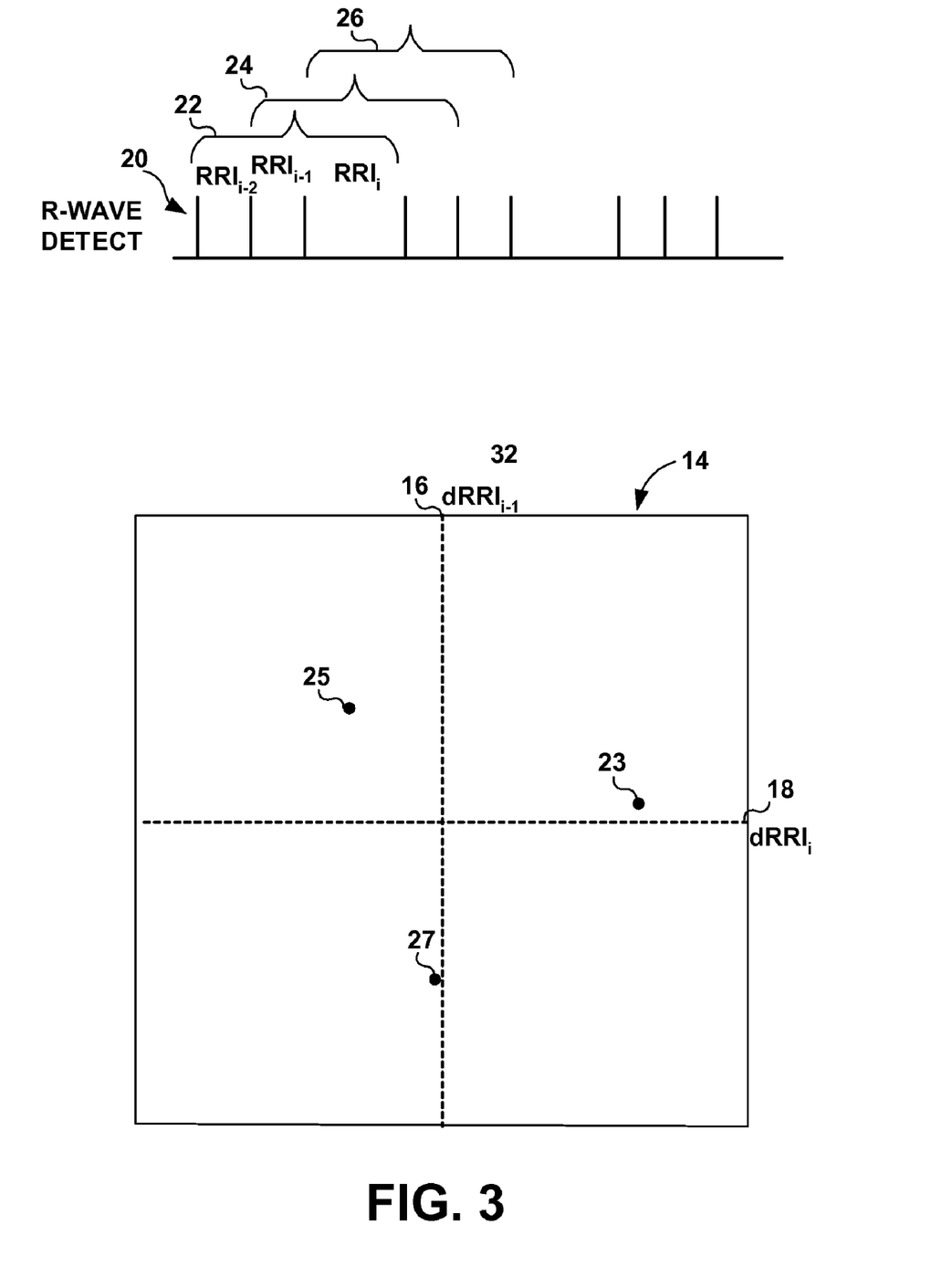
FIG. 3 illustrates the generation of a Lorenz scatter plot of ventricular cycle length data for use in detecting atrial arrhythmias.

FIG. 3 illustrates the generation of a Lorenz scatter plot of VCL data for use in detecting atrial arrhythmias. The differences between consecutive RR intervals ($\delta RRs$) are plotted for a time series of R-R intervals (RRIs). The Lorenz plot 14 is a Cartesian coordinate system defined by $\delta RR_i$ along the x-axis 18 and $\delta RR_{i-1}$ along the y-axis 16. As such, each plotted point in a Lorenz plot is defined by an x-coordinate equaling $\delta RR_i$ and a y-coordinate equaling $\delta RR_{i-1}$. $\delta RR_i$ is the difference between the $i^{th}$ RRI and the previous RRI, $RRI_{i-1}$. $\delta RR_{i-1}$ is the difference between $RRI_{i-1}$ and the previous RRI, $RRI_{i-2}$. As such, each data point plotted on the Lorenz plot 14 represents a VCL pattern relating to three consecutive VCLs: $RRI_i$, $RRI_{i-1}$ and $RRI_{i-2}$. As noted previously, VCL information is not limited to detection of R-waves and determination of RRIs. The terms RRI and $\delta RR_i$ as used herein refer generally to a measurement of VCL and the difference between two consecutive VCL measurements, respectively, whether the VCL measurements were derived from a series of R-wave detections from an EGM or ECG signal or another ventricular cycle event detection from any other physiological signal (e.g. a peak pressure determined from a pressure signal). For the sake of illustration, the embodiments described herein often refer to R-wave detections for performing VCL measurements and the determination of ($\delta RR_i$, $\delta RR_{i-1}$) points.

In FIG. 3, a series of R-wave events 20 are shown. In order to plot a point on the Lorenz plot area 14, a ($\delta RR_i$, $\delta RR_{i-1}$) point is determined by measuring successive RRIs determined from the R-wave events 20. In the example shown, a first series 22 of three consecutive RRIs ($RRI_{i-2}$, $RRI_{i-1}$ and $RRI_i$) provides the first data point on the Lorenz plot area 14. $\delta RR_{i-1}$, which is the difference between $RRI_{i-2}$ and $RRI_{i-1}$ is approximately 0. $\delta RR_i$, the difference between the $RRI_{i-1}$ and $RRI_i$, is a positive change. Accordingly, a ($\delta RR_i$, $\delta RR_{i-1}$) point 23 having a y-coordinate near 0 and a positive x-coordinate is plotted in the Lorenz plot 14, representing the first series 22.

The next series 24 of three RRIs provides the next ($\delta RR_i$, $\delta RR_{i-1}$) point 25 having a negative x-coordinate ($RRI_i$ being less than $RRI_{i-1}$) and a positive y-coordinate ($RRI_{i-1}$ being greater than $RRI_{i-2}$). This process of plotting ($\delta RR_i$, $\delta RR_{i-1}$) points continues with the three cycle series 26 providing data point 27 and so on.

Methods have been developed for detecting atrial arrhythmias based on the irregularity of ventricular cycles measured by RR intervals that exhibit discriminatory signatures when plotted in a Lorenz scatter plot such as the plot shown in FIG. 3. One such method is generally disclosed by Ritscher et al. in U.S. Pat. No. 7,031,765, incorporated herein by reference in its entirety. Another method is generally disclosed by Sarkar, et al. in U.S. Patent Publication No. 2006/0247547, also incorporated herein by reference in its entirety.

Figure 4:
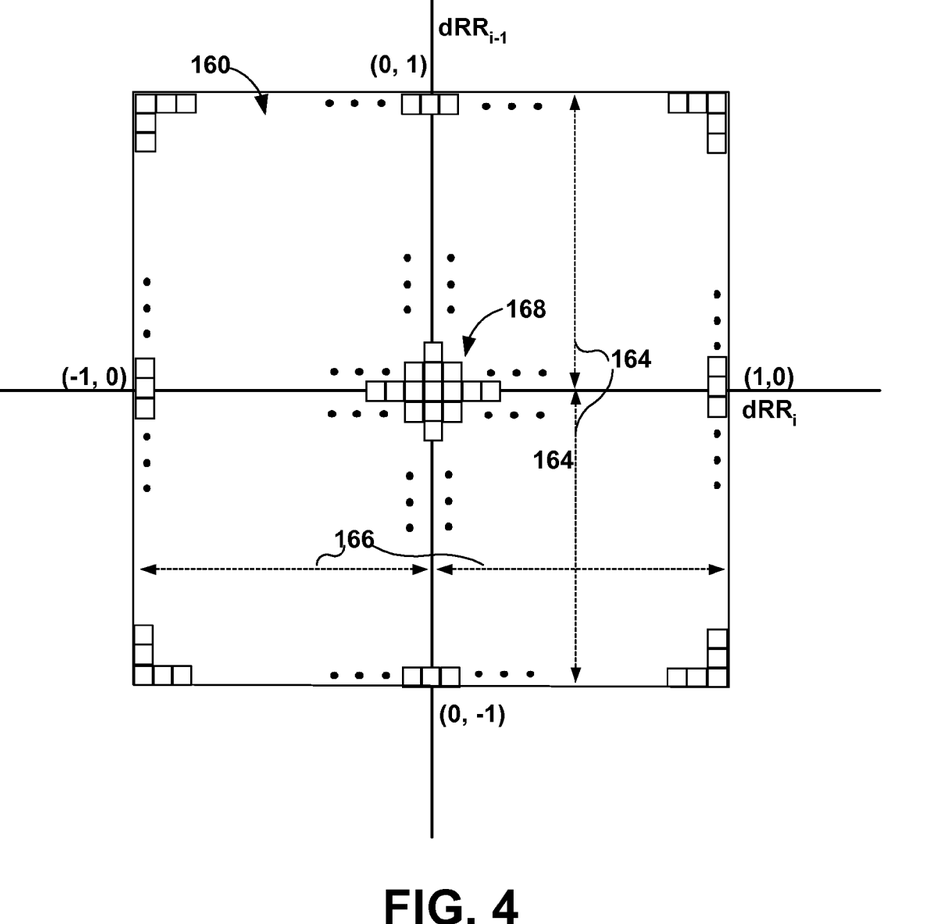
FIG. 4 is a diagram of a two-dimensional histogram representing the Lorenz plot area.

FIG. 4 is a diagram of a two-dimensional histogram representing the Lorenz plot area. Generally, the Lorenz plot area 14 shown in FIG. 3 is numerically represented by a two-dimensional histogram 160 having predefined ranges 166 and 164 in both positive and negative directions for the $\delta RR_i$ and $\delta RR_{i-1}$ coordinates, respectively. The two-dimensional histogram is divided into bins 168 each having a predefined range of $\delta RR_i$ and $\delta RR_{i-1}$ values. In previous atrial arrhythmia detection methods, the histogram range might extend from −1200 ms to +1200 ms for both $\delta RR_i$ and $\delta RR_{i-1}$ values, and the histogram range is divided into bins extending 7.5 ms in each of the two dimensions resulting in a 160×160 histogram. Any ($\delta RR_i$, $\delta RR_{i-1}$) values falling outside the range of the histogram, or outside a previously defined outlier boundary have been ignored for purposes of detecting atrial arrhythmias. When the ventricular rate is high, a metric of VCL variability derived from a Lorenz plot is suppressed since the sparseness of the data points during high ventricular rates will be reduced. This result can lead to false negative AF detections.

In accordance with one embodiment of the present invention, the ($\delta RR_i$, $\delta RR_{i-1}$) data points are normalized such that the two-dimensional histogram 160 is provided with a range of (−1, +1) in both x- and y-directions as shown in FIG. 4. All normalized $\delta RR_i$ values will fall within the histogram bin range so that there will be no ignored or outlying data points. Furthermore, normalization of the RRI data will eliminate suppression of VCL irregularity during high ventricular rates since the normalized data will be spread over more of the normalized plot area.

The $\delta RR_i$ values may be normalized using any of numerous normalization factors derived from the measured RRIs. In one embodiment, each $\delta RR_i$ value is divided by the maximum of the two measured RRIs used to compute the $\delta RR_i$, as shown by the following equations:

$$\delta RR_i = (RRI_n - RRI_{n-1})/\max(RRI_n, RRI_{n-1})$$

$$\delta RR_{i-1} = (RRI_{n-1} - RRI_{n-2})/\max(RRI_{n-1}, RRI_{n-2})$$

It is recognized that other normalization factors could be substituted such as a mean or average RRI or any other value derived from the RRIs measured during the data acquisition period.

In one embodiment, a 2D histogram is defined having a range of (−1, +1) in both x- and y-directions. The histogram may include about 40 bins along each axis for a total of 160 bins, each bin having a range of about 0.05 in each x- and y-direction.

Figure 5:
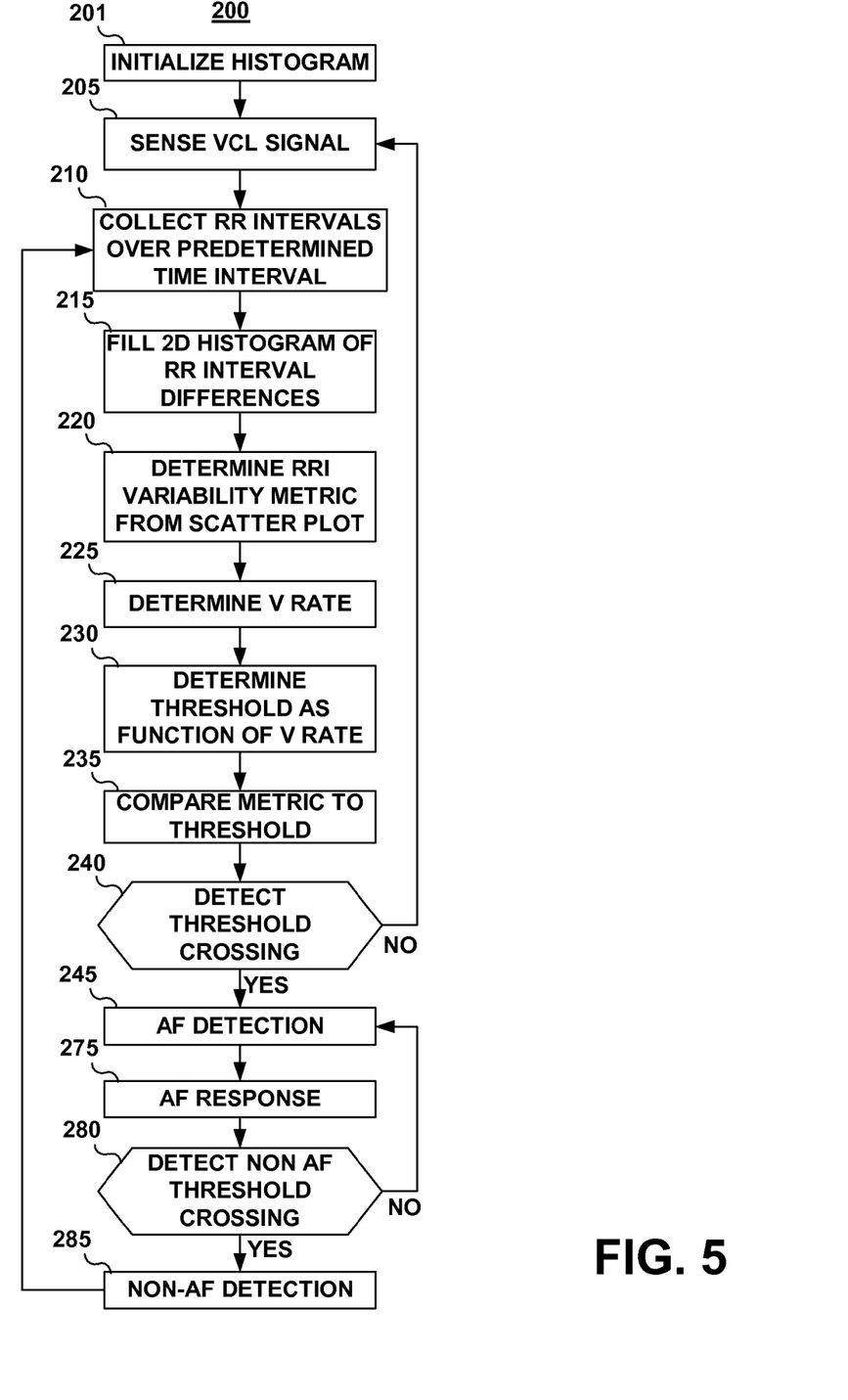
FIG. 5 is a flow chart of a method for detecting atrial fibrillation (AF).

FIG. 5 is a flow chart of a method for detecting atrial fibrillation. Flow chart 200 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern ICD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 200 is directed to atrial fibrillation (AF) detection; however it is recognized that aspects of the invention may be applied to detection of other atrial arrhythmias, such as atrial flutter. At block 201, a histogram is initialized by defining the number of histogram bins for each coordinate axes and corresponding bin ranges. A counter for each histogram bin is set to zero. At block 205, a physiological signal containing VCL information is sensed. At block 210 the VCL intervals, which may be RR intervals, are collected over a predetermined data acquisition time interval, for example for 2 minutes. At block 215, the histogram is filled, corresponding to a Lorenz scatter plot of the successive RR interval differences. As described previously, a 2D scatter plot is generated wherein each point is defined by an x-coordinate corresponding to the difference between an RRI and the previous RRI and the y-coordinate corresponding to the difference between the previous RRI and the next previous RRI. The histogram is filled by incrementing a counter for the histogram bin which corresponds to the coordinate values of each normalized ($\delta RR_i$, $\delta RR_{i-1}$) data point. The methods described herein are generally implemented using a 2D histogram, however aspects of the invention may alternatively be implemented in methods using 1D or higher dimensional scatter plots of VCL data.

At block 220 an RRI variability metric is determined from the scatter plot. Generally, the more histogram bins that are occupied, i.e. the more sparse the distribution of ($\delta RR_i$, $\delta RR_{i-1}$) points, the more irregular the VCL during the data acquisition time period. As such, a metric of the RRI variability can be used for detecting atrial fibrillation, which is associated with highly irregular VCL. In one embodiment, an RRI variability metric for detecting AF, referred to as an AF score, is defined by the equation:

$$AF\ score = LowCount + NonZeroCount - MaxBinCount$$

wherein LowCount is the number of histogram bins having a count less than a predetermined maximum, i.e. relatively few ($\delta RR_i$, $\delta RR_{i-1}$) data points falling into those bins. In one embodiment, LowCount is the number of histogram bins having a count of at least one but less than six. NonZeroCount is the number of occupied bins, i.e. the number of bins having a count of at least one. A high number of occupied bins and a high number of bins having a low count are both positive predictors for a sparse distribution of ($\delta RR_i$, $\delta RR_{i-1}$) points, and therefore positive predictors for AF. A bin having a relatively high count, indicating clustering of ($\delta RR_i$, $\delta RR_{i-1}$) points, is a negative predictor of AF. As such, MaxBinCount is the highest histogram bin count at the end of the data acquisition time interval. MaxBinCount is subtracted from the positive predictors of AF.

The AF score will be compared to a threshold for detecting AF at block 235. According to one embodiment of the invention, the threshold is determined as a function of the ventricular rate. During an extended episode of low ventricular rate, the number of RRI measured within the predetermined time window will be reduced. When a detection threshold is fixed, the detection sensitivity will be reduced during low ventricular rates compared to during high ventricular rates. As such, a variable detection threshold is defined as a function of the ventricular rate.

Figure 6:
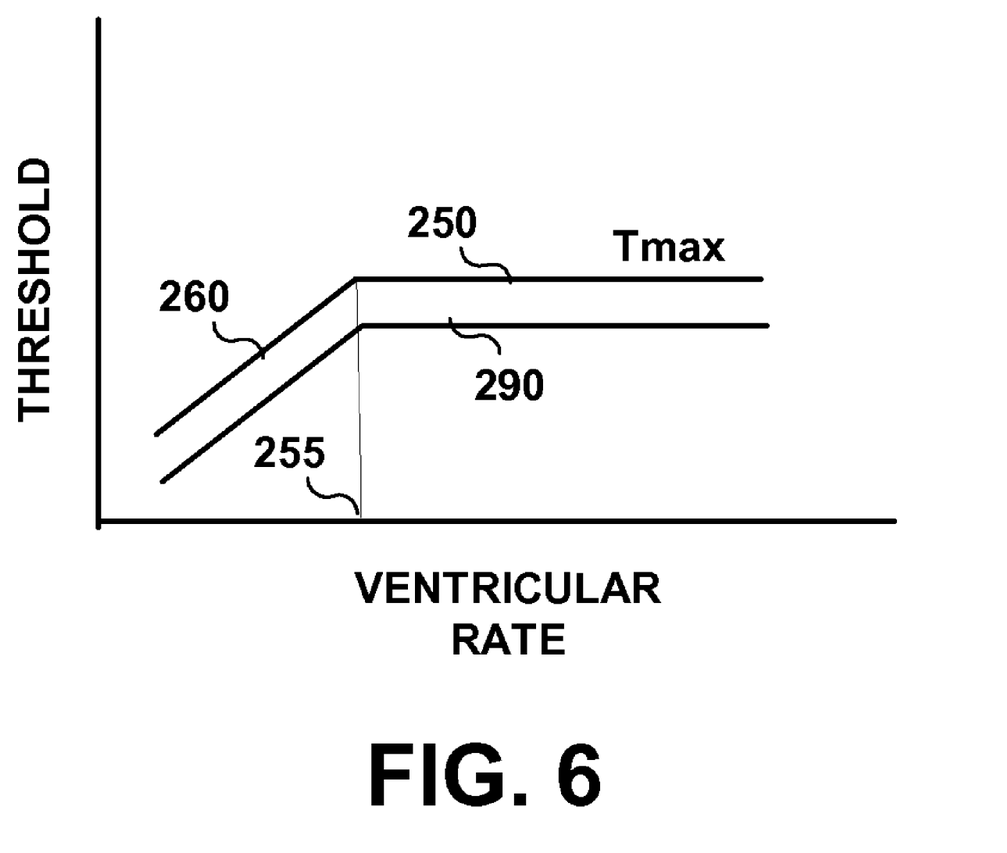
FIG. 6 is a plot of an AF detection threshold as a function of ventricular rate.

FIG. 6 is a plot of an AF detection threshold as a function of ventricular rate. In one embodiment, an AF detection threshold 260 is defined as a proportion of a maximum threshold 250 when the number of ventricular cycles during the data acquisition time interval is less than an expected or minimum number of ventricular cycles 255. The proportion may be the ratio of the number of ventricular cycles occurring to the expected minimum number of ventricular cycles:

$$\text{Threshold} = T\text{max} * (\text{actual } VCLs / \text{expected } VCLs)$$

Wherein Tmax is a predefined maximum threshold, actual VCLs is the actual number of VCLs during the data acquisition time period and expected VCLs is a predetermined minimum number of VCLs at which Tmax is used.

If the number of ventricular cycles occurring during the predetermined time interval is equal to or greater than the expected number of VCLs 255, the AF detection threshold is set as the maximum threshold 250. It is recognized that other methods may be used for setting a detection threshold as a function of ventricular rate.

At block 230 of FIG. 5, the threshold is determined as a function of ventricular rate. At block 235, the RRI variability metric is compared to the threshold. If a threshold crossing is detected, as determined at block 240, AF is detected at block 245. An AF response may be provided at block 245. The AF response may be to generate a patient alarm or deliver or adjust a therapy. The RRI measurements continue to be performed after an AF detection to fill the histogram during the next data acquisition time interval. After each data acquisition interval, the RRI variability metric is determined and the histogram bins are re-initialized to zero for the next data acquisition interval. The new RRI variability metric determined at the end of each data acquisition interval is used to determine if the AF episode is sustained or terminated.

In order to prevent frequent transitions between an AF detection and a non-AF detection, the AF detection threshold is provided with a hysteresis such that the RRI variability metric must cross a lower threshold for detecting non-AF than for detecting AF. Referring again to FIG. 6, a non-AF detection threshold 290 may be set as a percentage, for example 80%, of the AF detection threshold 260.

At decision block 280, the most recent RRI variability metric, determined after each data acquisition interval after the AF detection is made, is compared to the lower, non-AF detection threshold. If the RRI variability metric remains greater than the non-AF detection threshold, the AF detection is sustained at block 245. The AF response at block 275 is generally performed only in response to the initial AF detection and not repeated as long as the AF detection is sustained. If the RRI variability metric falls below the lower threshold, as determined at block 280, non-AF detection is declared at block 285. Method 200 returns to block 210 to continue monitoring the RRI variability metric for detecting the next AF episode.

Thus, a device and method for detecting atrial arrhythmias in response to VCL variability measurements have been presented in the foregoing description with reference to specific embodiments. It is appreciated that various modifications to the referenced embodiments may be made without departing from the scope of the invention as set forth in the following claims.

The invention claimed is:

1. A method for detecting atrial arrhythmias, comprising:
   sensing a signal including ventricular cycle length information in a patient;
   determining a ventricular cycle length occurring during a predetermined time period;
   determining a difference between successive ventricular cycle lengths occurring during the predetermined time period;
   storing the difference as a data point in a histogram;
   determining a metric of variability of at least two data points of the histogram;
   determining a number of ventricular cycle lengths occurring during the predetermined time period;
   determining a first threshold in response to the determined number of ventricular cycle lengths; and
   detecting an atrial arrhythmia in response to the metric crossing the first threshold.

2. A method according to claim 1 wherein storing each succeeding difference includes normalizing the difference by a selected difference.

3. A method according to claim 2 wherein the selected difference is a maximum one of each ventricular cycle length difference and a preceding ventricular cycle length difference.

4. A method according to claim 1 wherein determining the threshold includes computing a proportion of a maximum threshold, wherein the proportion corresponds to the number of ventricular cycle lengths occurring during the predetermined period of time.

5. A method according to claim 1 further comprising detecting no atrial arrhythmia in response to the metric crossing a second threshold after crossing the first threshold.

6. A method according to claim 5 wherein the second threshold being less than the first threshold.

7. A method according to claim 6 wherein the second threshold being a percentage of the first threshold.

8. A computer-readable medium for storing a set of instructions which when implemented in a system cause the system to:
   sense a signal including ventricular cycle length information in a patient;
   determine each ventricular cycle length occurring during a predetermined time period;
   determine each difference between successive ventricular cycle lengths occurring during the predetermined time period;
   store each succeeding difference as a data point in a histogram;
   determine a metric of variability of the data points of the histogram;
   determine a number of ventricular cycle lengths occurring during the predetermined period of time;
   determine a first threshold in response to the determined number of ventricular cycle lengths; and
   detect an atrial arrhythmia in response to the metric crossing the first threshold.

9. A computer-readable medium according to claim 8 wherein instructions for storing each succeeding difference include instructions for normalizing the difference by a selected difference.

10. A computer-readable medium according to claim 9 wherein the selected difference is a maximum one of each ventricular cycle length difference and a preceding ventricular cycle length difference.

11. A computer-readable medium according to claim 8 wherein instructions for determining the threshold include instructions for computing a proportion of a maximum threshold, wherein the proportion corresponds to the number of ventricular cycle lengths occurring during the predetermined period of time.

12. A computer-readable medium according to claim 8 further comprising instructions for causing the system to detect no atrial arrhythmia in response to the metric crossing a second threshold after crossing the first threshold.

13. A computer-readable medium according to claim 12 wherein the second threshold being less than the first threshold.

14. A computer-readable medium according to claim 13 wherein the second threshold being a percentage of the first threshold.

15. A medical device for detecting atrial arrhythmias, comprising:
  a sensor for sensing a signal including ventricular cycle length information in a patient;
  memory allocated for storing ventricular cycle length data in a histogram; and
  a control module coupled to the sensor and the memory, the control module configured to determine from the signal each difference between successive ventricular cycle lengths occurring during a predetermined time period, store each succeeding difference as a data point in the histogram, determining a metric of variability of the data points of the histogram, and detect an atrial arrhythmia in response to the metric crossing a first threshold,
  wherein the first threshold being determined by the control module in response to the number of ventricular cycle lengths occurring during the predetermined time period.

16. A medical device according to claim 15 wherein storing each succeeding difference includes normalizing the difference by a selected difference.

17. A medical device according to claim 16 wherein the selected difference is a maximum one of each ventricular cycle length difference and a preceding ventricular cycle length difference.

18. A medical device according to claim 15 wherein determining the threshold includes computing a proportion of a maximum threshold, wherein the proportion corresponds to the number of ventricular cycle lengths occurring during the predetermined period of time.

19. A medical device according to claim 15 wherein the control module being further configured to detect no atrial arrhythmia in response to the metric crossing a second threshold after crossing the first threshold.

20. A medical device according to claim 19 wherein the second threshold being less than the first threshold.

21. A medical device according to claim 19 wherein the second threshold being a percentage of the first threshold.

* * * * *